US00PP18690P3

(12) United States Plant Patent

Bacon et al.

(10) Patent No.: US PP18,690 P3

(45) Date of Patent: Apr. 1, 2008

(54) PLUM TREE NAMED 'SUPLUMTHIRTYSEVEN'

(50) Latin Name: *Prunus salicina*
Varietal Denomination: Sulplumthirtyseven

(75) Inventors: Terry A. Bacon, Bakersfield, CA (US); David W. Cain, Bakersfield, CA (US)

(73) Assignee: Sun World International, LLC, Bakersfield, CA (US)

( * ) Notice: Subject to any disclaimer, the term of this patent is extended or adjusted under 35 U.S.C. 154(b) by 35 days.

(21) Appl. No.: 11/378,499

(22) Filed: Mar. 17, 2006

(65) Prior Publication Data

US 2007/0220638 P1 Sep. 20, 2007

(51) Int. Cl.
*A01H 5/00* (2006.01)

(52) U.S. Cl. ..... Plt./184

(58) Field of Classification Search ..... Plt./184
See application file for complete search history.

(56) References Cited

U.S. PATENT DOCUMENTS

PP7,443 P * 2/1991 Weinberger et al.

* cited by examiner

*Primary Examiner*—Kent Bell
(74) *Attorney, Agent, or Firm*—Knobbe Martens Olson & Bear LLP

(57) ABSTRACT

A new and distinct plum tree variety, *Prunus salicina,* cv. 'Suplumthirtyseven' characterized by heavy and consistent production of early-season yellow-fleshed purple-black plums that have aromatic sweet flavor, excellent juiciness, and high sugar content (17 degrees brix). The combined traits of the new variety constitute superior quality relative to other commercial plum varieties ripening in 'Black Beaut' (unpatented) ripening season in the San Joaquin Valley, Calif.

1 Drawing Sheet

Figure 1:
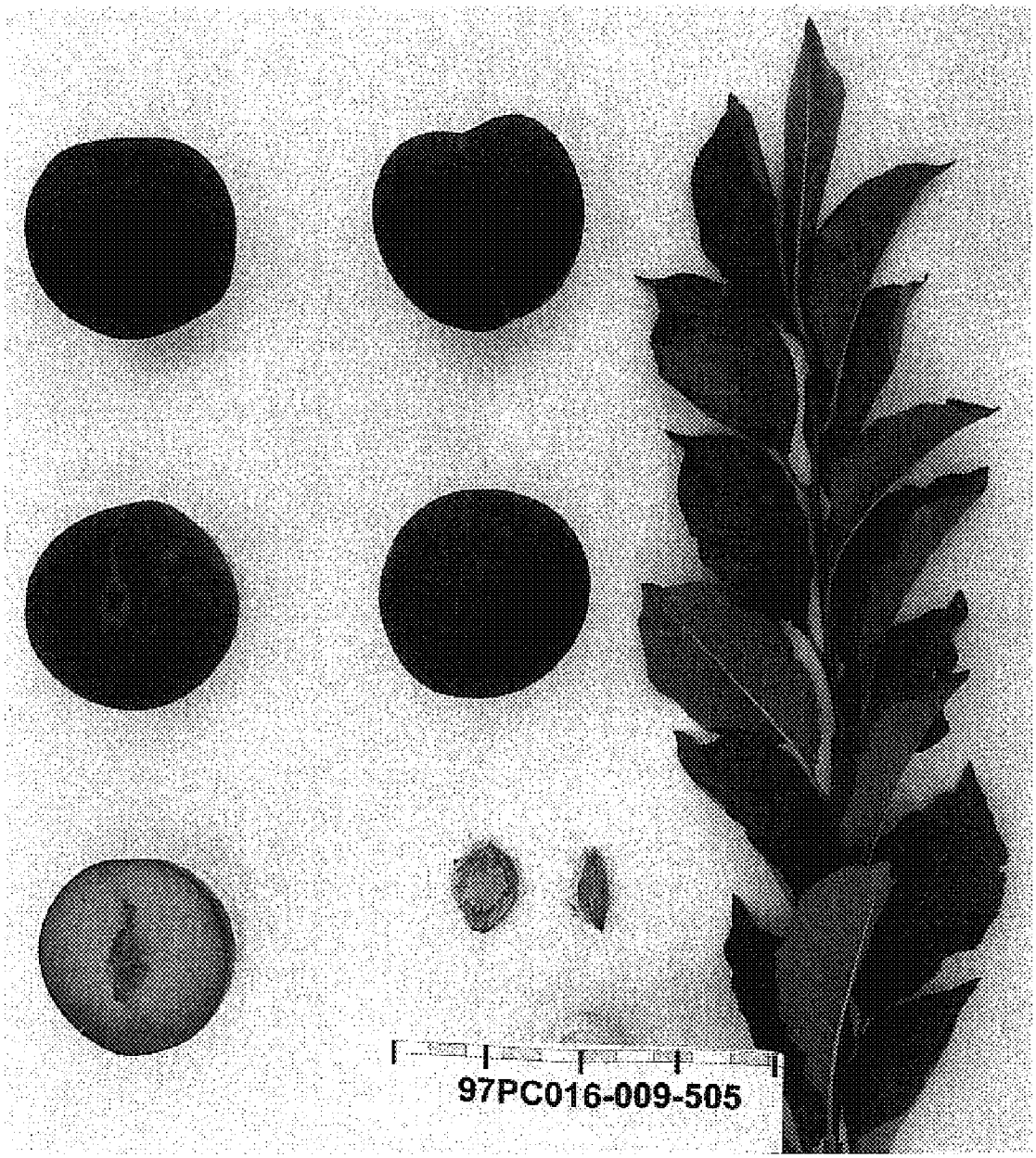

Latin name of the genus and species claimed: *Prunus salicina.*

Variety denomination: 'Suplumthirtyseven'.

BACKGROUND AND SUMMARY OF THE INVENTION

This invention relates to the discovery and asexual propagation of a new and distinct variety of plum, *Prunus salicina* cv. 'Suplumthirtyseven.' The new variety was first hybridized by David Cain and selected by Terry Bacon as breeder number: '97PC016-009-505.' The new variety was first evaluated by Terry Bacon near Wasco, Kern County, Calif. The new variety 'Suplumthirtyseven' originated by hybridization.

The new variety 'Suplumthirtyseven' has several traits that, when combined, result in a higher quality than other commercial plum varieties that ripen in 'Black Beaut' (unpatented) ripening season in the San Joaquin Valley, Calif. The new variety 'Suplumthirtyseven' is characterized by heavy and consistent production of early-season yellow-fleshed purple-black plums. The plums have an aromatic sweet flavor, excellent juiciness, and a high sugar content (approximately 17 degrees brix).

The seed parent of the new variety 'Suplumthirtyseven' is the unpatented breeding selection '92PC003-126-118' that was selected from a progeny of '401-048' (U.S. Plant Pat. No. 7,443) that was open pollinated with pollen of an unknown breeding selection plum. The hybridization of the seed parent occurred in March 1997, with the date of planting of the new plum variety 'Suplumthirtyseven' being February 1998, and the date of first flowering being March 2000. The new plum variety 'Suplumthirtyseven' was first asexually propagated by Terry Bacon near Wasco, Kern County, Calif. in 2001, by budding onto 'Nemared' (unpatented) rootstock.

The new variety 'Suplumthirtyseven' is distinguished from its seed parent, '92PC003-126-118' in that the new variety ripens in late May in Waco, Calif., approximately six weeks before the seed parent ripens. The new plum variety 'Suplumthirtyseven' also has a higher sugar level of approximately 17 degrees brix while the seed parent has a brix level of approximately 14 degrees.

The new plum variety 'Suplumthirtyseven' most closely resembles the commercial variety, 'Santa Rosa' (unpatented) but has a larger fruit size (approximately 61 mm) and purple-black skin, while the fruit of 'Santa Rose' is approximately 54 mm diameter and has red skin. The new plum variety 'Suplumthirtyseven' also ripens approximately 3 weeks before 'Santa Rosa.'

In comparison to the commercially grown variety 'Black Beaut' (unpatented), the new variety ripens approximately 7 days earlier than 'Black Beaut' and has a larger size fruit (approximately 61 mm) compared with the fruit of 'black Beaut' (approximately 56 mm). The new plum variety 'Suplumthirtyseven' also has a higher sugar content (approximately 17 degrees brix) compared with approximately 15 degrees brix for 'Black Beaut.'

The new variety 'Suplumthirtyseven' has been shown to maintain its distinguishing characteristics through successive asexual propagations by, for example, budding onto 'Nemared' (unpatented) rootstock.

BRIEF DESCRIPTION OF THE PHOTOGRAPH

The accompanying color photographic illustration shows typical specimens of the foliage and fruit of the present new plum variety 'Suplumthirtyseven.' The illustration shows the upper and lower surface of the leaves, an exterior and sectional view of a fruit divided across its suture plane to show flesh color, pit cavity and the stone remaining in place. The photographic illustration was taken shortly after being picked (shipping ripe) and the colors are as nearly true as is reasonably possible in a color representation of this type.

DETAILED BOTANICAL DESCRIPTION OF THE INVENTION

Throughout this specification, color names beginning with a small letter signify that the name of that color, as used in common speech is aptly descriptive. Color names beginning with a capital letter designate values based upon the R.H.S. Colour Chart published by The Royal Horticultural Society, London, England.

The descriptive matter which follows pertains to 5 year old 'Suplumthirtyseven' plants of Nemared rootstock, grown in the vicinity of Wasco, Kern County, Calif., during 2005, and is believed to apply of plants of the variety grown under similar conditions of soil and climate elsewhere.

TREE

General: (Measurements taken on 5 year old tree on Nemared rootstock unless otherwise noted.)

*Size.*—Medium. Normal for most plum varieties. Reaches a height of approximately 3 meters and a diameter of approximately 5 meters, including normal pruning.

*Vigor.*—Moderately vigorous; growth of approximately 1.5 to 2 meters in height the first growing season.

*Growth.*—Upright-spreading.

*Productivity.*—Productive. Fruit set is usually two or more times desired amount for marketable size fruit. Thinning and spacing of fruit is necessary.

*Form.*—Vase formed.

*Bearer.*—Regular. No alternate bearing observed.

*Fertility.*—Unknown. Should be planted with another variety to ensure consistent production.

*Canopy density.*—Medium-dense. Pruning is required to open tree vase shape, allowing more sunlight to center of tree.

*Hardiness.*—Hardy in all fruit growing areas of California. Winter chilling requirement is approximately 650 hours at or below approximately 7.2° C.

*Disease resistance/susceptibility.*—No specific testing for relative plant disease resistance/susceptibility has been designed. Under close observation in Kern Country, Calif., no particular plant/fruit disease resistance/susceptibility has been observed.

Trunk: (Measurements at 30 cm above soil line.)

*Diameter.*—Approximately 18 cm, varies with soil type, fertility, climatic conditions and cultural practices.

*Texture.*—Medium shaggy, increases with age of tree.

*Trunk color.*—About Grey-brown 199B to Brown 200B, becomes darker with age.

Branches: (Measurements at approximately 90 cm above soil line.)

*Size.*—Diameter ranged from approximately 7 cm to approximately 9 cm. Average length is approximately 2 meters.

*Texture.*—Smooth on first year wood, increasing roughness with tree age.

*Color.*—Branches vary from about Grey-brown 199B to Brown 200B.

*Lenticels.*—Number: Numerous. Color: About Grey-brown 199B. Length: Approximately 3 mm. Width: Approximately 2 mm.

Flowering shoots: (Data taken in July at midpoint of current-season growth.)

*Size.*—Average diameter approximately 5 mm. Average length is approximately 40 cm.

*Color.*—Topside: About Yellow-green 152A. Underside: About Yellow-green 146B.

*Flowering shoot lenticels.*—Plentiful.

*Flowering shoot leaf buds.*—Shape: Obovate. Width: Approximately 1.5 mm. Length: Approximately 2.1 mm. Color: About Greyed-orange 177A.

*Flowering shoot flower buds.*—Shape: Elliptic. Width: Approximately 1 mm. Length: Approximately 1.8 mm. Color: About Greyed-orange 177A. Number Per Node: Usually 2.

FOLIAGE

Leaves: (Data taken in July on fully expanded leaf at midpoint of current-season growth.)

*Size.*—Average length: Approximately 90 mm with petiole. Average width: Approximately 40 mm.

*Thickness.*—Medium.

*Color.*—Upper surface: About Yellow-green 147A. Lower surface: About Yellow-green 147B.

*Form.*—Elliptic.

*Tip.*—Cuspidate.

*Base.*—Cuneate.

*Margin.*—Finely serrated.

*Venation.*—Pinately net veined.

*Surface texture.*—Smooth.

Petiole:

*Average length.*—Approximately 12 mm.

*Average diameter.*—Approximately 1.5 mm.

*Color.*—About Yellow-green 146D.

Leaf stipules:

*Number.*—1 per leaf bud when present.

*Length.*—Approximately 3 mm.

Leaf glands:

*Form.*—Globose.

*Number.*—Varies from 0 to 2.

*Position.*—Opposite on upper portion of petiole and base of leaf blade.

*Average size.*—Approximately 0.8 mm by approximately 0.8 mm.

*Color.*—About Yellow-green 146D.

FLOWERS (Fully opened)

General:

*Flower blooming period.*—First bloom: Approximately Feb. 20, 2005. Full bloom: Approximately Feb. 24, 2005.

*Size.*—Average depth: Approximately 10 mm. Average diameter: Approximately 25 mm.

*Flower aroma.*—Very slight.

Peduncle:

*Length.*—Approximately 10 mm.

*Diameter.*—Approximately 1 mm.

*Color.*—About Yellow-green 144B.

Petals:

*Number.*—5.

*Arrangement.*—Overlapping slightly.

*Length.*—Approximately 10 mm.

*Diameter.*—Approximately 10 mm.
*Shape.*—Circular.
*Apex shape.*—Rounded.
*Base shape.*—Narrows at point of attachment.
*Color.*—Upper surface: About White 155D. Lower surface: About White 155D.
*Surface texture.*—Smooth.
*Margins.*—Slightly undulating.

Sepals:
*Number.*—5.
*Length.*—Approximately 3 mm.
*Diameter.*—Approximately 2 mm.
*Shape.*—Elliptic.
*Color.*—About Yellow-green 144A.
*Surface texture.*—Smooth.

Stamens:
*Number.*—Ranges from approximately 20 to approximately 30, average 25.
*Average length.*—Approximately 7 mm.
*Filament color.*—About White 155.
*Anther color.*—About Greyed-orange 167A.
*Pollen color.*—About Greyed-orange 167A.

Pistil:
*Apex.*—Rounded.
*Margins.*—Finely serrated.
*Number.*—Usually one, occasionally two.
*Average length.*—Approximately 9 mm.
*Ovary diameter.*—Approximately 0.5 mm.
*Pubescence.*—None.
*Stigma extension in comparison to anthers.*—Level with or slightly above anthers.

FRUIT

General: (Data taken at firm-ripe on mature tree managed to obtain maximum quality under conditions stated in Description of Variety.)
*Harvest.*—Date of first pick: Approximately May 24, 2005. Date of last pick: Approximately Jun. 1, 2005.

Size:
*Length* (*stem end to apex*).—Approximately 63 mm.
*Diameter in Line with suture plane.*—Approximately 61 mm.
*Diameter perpendicular to suture plane.*—Approximately 61 mm.
*Average weight.*—Approximately 112 gm.

Form:
*Viewed from apex.*—Rounded.
*Viewed from side, facing suture.*—Rounded.
*Viewed from side, perpendicular to suture.*—Rounded.

Apex shape: Flattened.

Fruit stem-end cavity depth: Shallow (approximately 7 mm).

Fruit stem:
*Length.*—Approximately 7 mm.
*Diameter.*—Approximately 2 mm.
*Color.*—About Green 143C.

Fruit skin:
*Thickness.*—Medium.
*Adherence to flesh.*—Tenacious.
*Surface texture.*—Smooth.
*Pubescence.*—None.
*Bloom.*—Moderate amount.
*Ground color.*—Not visible.
*Overcolor.*—About Greyed-purple 187A.
*Taste.*—Mildly tart.

Flesh:
*Ripens.*—Evenly.
*Texture.*—Juicy, fine.
*Fibers.*—Few.
*Flavor.*—Mildy-sweet.
*Brix.*—Approximately 17 degrees.
*Juice.*—Plentiful.
*Aroma.*—Noticeable.
*Color.*—The flesh is a whitish pink color (about Orange 29C), becoming more reddish as it ripens. When ripe, about Orange-red 34B.

Fruit use: Dessert. Market, local and long distance.

Fruit shipping and keeping quality: Good, holds well in cold storage for approximately 6 weeks and maintains good firmness and eating quality, minimal bruising and scarring in packing and shipping trails. Stone: (measurements taken on dried stones.)
*Stone Freeness.*—Clingstone.
*Stone size.*—Length: Approximately 24 mm. Diameter in line with suture plane: Approximately 18 mm. Diameter perpendicular to suture plane: Approximately 9 mm.
*Stone farm.*—Viewed from side: Eliptical oblong. Viewed from stem end: Flattened, symmetrical.
*Stone shape.*—Base shape: Oblique and retuse, symmetrical at stem attachment. Apex shape: Rounded with a small, sharp point.
*Stone surface.*—Irregularly furrowed near base, lightly ridged throughout, lightly pitted throughout.
*Stone halves.*—Nearly equal.
*Stone ridges.*—1 on each side of the suture, small and narrower beginning at the base and extending throughout the length of the stone.
*Stone outgrowing keel.*—Absent.
*Stone Tendency to split.*—None.
*Stone color.*—About Greyed-orange 164C when dried.

What is claimed is:

1. A new and distinct plum tree as herein described and illustrated.

* * * * *